(12) United States Patent
Rochat

(10) Patent No.: US 6,273,264 B1
(45) Date of Patent: Aug. 14, 2001

(54) DEVICE AND METHOD FOR SEPARATING PARTICLES CONTAINED IN A FLUID

(76) Inventor: Jean Denis Rochat, En-Tenet, 1272 Genolier (CH)

(*) Notice: Subject to any disclaimer, the term of this patent is extended or adjusted under 35 U.S.C. 154(b) by 0 days.

(21) Appl. No.: 09/405,902

(22) Filed: Sep. 24, 1999

Related U.S. Application Data

(63) Continuation-in-part of application No. PCT/EP98/01685, filed on Mar. 23, 1998.

(30) Foreign Application Priority Data

Mar. 24, 1997 (DE) .............................. 197 12 242

(51) Int. Cl.⁷ ........................................ B03B 5/66
(52) U.S. Cl. .................. 209/156; 209/132; 209/155; 209/172; 209/172.5; 210/600; 210/739; 210/767
(58) Field of Search ................... 209/132, 155, 209/156, 172, 172.5; 210/600, 739, 767

(56) References Cited

U.S. PATENT DOCUMENTS

| 2,967,618 | 1/1961 | Vane . |
| 4,170,555 | 10/1979 | Vicard . |
| 5,961,841 | * 10/1999 | Bowers ................................ 210/739 |

FOREIGN PATENT DOCUMENTS

| 19 45 922 | 4/1971 | (DE) . |
| 2 646 104 | 10/1990 | (FR) . |
| 2 293 993 | 4/1996 | (GB) . |
| WO 93 08892 | 5/1993 | (WO) . |

* cited by examiner

Primary Examiner—Donald P. Walsh
Assistant Examiner—Mark J. Beauchaine
(74) Attorney, Agent, or Firm—Henderson & Sturm LLP

(57) ABSTRACT

A device for separating dense particles contained in blood or one or more proteins contained in blood plasma by utilizing a separating arrangement. The separation arrangement includes a feed duct, at least two discharge ducts, a pump for producing a pressure in order to introduce the blood or blood plasma into the separating device, a measuring device provided with the discharge ducts, and a control arrangement connected to the measuring device. The separation arrangement also includes a respective arrangement changing the cross section of at least one of the two discharge ducts and connected to the control arrangement.

20 Claims, 2 Drawing Sheets

DEVICE AND METHOD FOR SEPARATING PARTICLES CONTAINED IN A FLUID

This is a continuation-in-part, of co-pending PCT Application Serial No. PCT/EP98/01685, filed on Mar. 23, 1998, entitled DEVICE AND METHOD FOR SEPARATING PARTICLES CONTAINED IN A FLUID, the disclosure of which in its entirety is incorporated by reference thereto herein.

BACKGROUND OF THE INVENTION

1. Field of the Invention

The present invention concerns a device and a method for separating particles contained in a fluid by means of a separating arrangement, which has at least one feed duct and at least two discharge ducts, said separating arrangement having a measuring device for sensing the separation level and provided with the discharge ducts, a control arrangement connected to the measuring device and comprising at least one respective arrangement for changing the cross section of at least one of the discharge ducts, said respective arrangement being connected to the measuring device.

The device and the method are suitable in particular for the treatment of biological fluids, such as milk or blood for example, being known in the latter case by the term plasmapheresis. This is understood to mean the mechanical separation of solid blood constituents and plasma after blood has been taken, plasmapheresis usually being carried out by means of a separating arrangement having a centrifuge.

2. Description of the Prior Art

There are numerous devices for automated blood donation, so-called haemapheresis, with which the required blood components, such as erthrocytes, thrombocytes, leucocytes, plasma etc., can be specifically collected, all of which devices operate on the centrifugal principle and have not only a considerable space requirement but also a high weight, of the order of magnitude of 20 to 200 kg, and are correspondingly expensive. These cell separators, which are used for removing whole blood, also require an extracorporeal amount of blood of the order of magnitude of 500 ml, it being important not to exceed a maximum throughflow in order to ensure satisfactory functioning of the centrifuge used for the separation.

BRIEF SUMMARY OF THE INVENTION

The object of the invention is to provide a device for separating particles contained in a fluid which is particularly simple in construction, has a high separating efficiency and causes considerably lower production and operating costs, as well as to specify an associated method.

Another object of the invention is to eliminate as many pumps as possible, preferably all but the one feeding pump upstream of the device, and to replace them by proportional valves which have a very short reaction time and are cheap.

On the basis of a device of the type specified more precisely at the beginning, this object is achieved by a device for separating dense particles contained in blood or one or more proteins contained in blood plasma by means of a separating arrangement which has the following components:

one feed duct, at least two discharge ducts, a pump for producing a pressure in order to introduce the blood or blood plasma into the separating device, a measuring device provided with the discharge ducts, a control arrangement connected to the measuring device, and a respective arrangement changing the cross section of at least one of the two discharge ducts and connected to the control arrangement.

The respective arrangement may change the cross section of one of the two discharge ducts or of both discharge ducts.

As a measuring device, a device sensing the separation level, such as an optical device can be used.

The device according to the invention, which is suitable for the treatment of a wide range of biological or non-biological fluids and serves in particular for the treatment of blood, allowing thrombocyles and plasma to be collected at the same time, has the advantage of a considerably lower space requirement.

With such a device, most of the pumps are eliminated, especially all pumps within the circuit or on the discharge side, to be replaced by rapid and cheap arrangement, such as valves.

The same object is achieved by a method for separating dense particles contained in blood or one or more proteins contained in blood plasma using a device, which has the following method steps the whole blood or the plasma is introduced into the separating device through the feed duct at a pressure produced by the pump, the degree of separation is established by means of the measuring device, the control arrangement brings about a change in the passage cross section of one or both discharge ducts with the aid of the arrangement changing the cross section of the discharge ducts if the limit between the dense particles and the blood or the proteins of plasma shifts so that it is ensured that the amount of blood or plasma fed in is equal to the sum of the amounts of the constituents emerging from the two discharge lines, and a high degree of separation is thus maintained.

In a first embodiment of the invention, the regulation device is, instead of the previously customary centrifuge, associated with a stationary hollow chamber, into one end of which the fluid is introduced tangentially at a given rate in such a way that the desired separation is brought about by the centrifugal forces occurring on the inside wall of the hollow chamber with the associated laminar flow, so that the dense particles contained in the fluid can be removed at the other end of the hollow chamber through the one discharge duct, while the fluid itself, in particular plasma, is removed through the other discharge duct. The laminar flow of the blood produces a better separation and less damage to the dense blood cells than in the case of separation by means of a centrifuge, provided that a minimum throughflow and a minimum tangential rate are maintained.

The dimensions of the hollow chamber, which in particular is cylindrical, of the order of magnitude of about 10 mm in diameter and 10 mm in length, require little constructional expenditure and allow a drastic reduction in production costs.

In a second embodiment of the invention, the regulation device is associated with other type of separating devices, such as those described in my co-pending European Patent Applications No. EP 99810294.1 and EP 99810295.8, contents of which are incorporated herein by way of reference.

BRIEF DESCRIPTION OF THE SEVERAL VIEWS OF THE DRAWINGS

The invention is explained more precisely below, in a first embodiment, with reference to the drawing, in which advantageous exemplary embodiments are represented and in which.

DETAILED DESCRIPTION OF THE INVENTION

Figure 1:
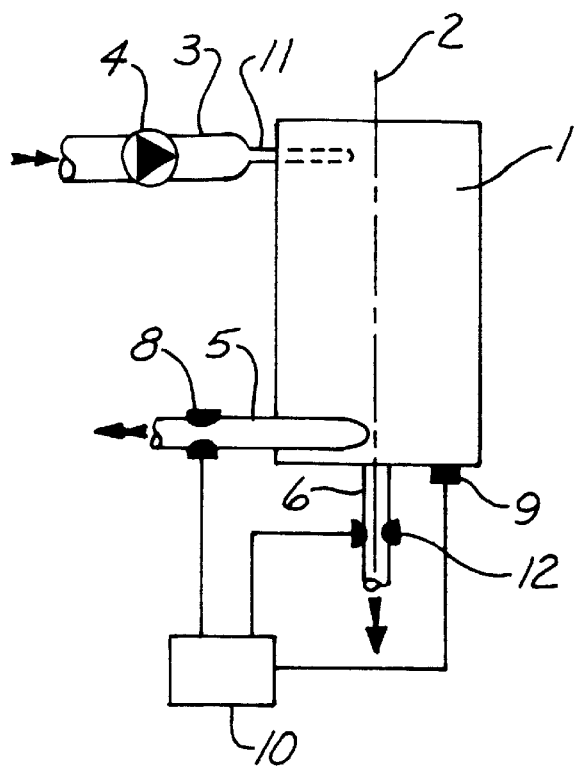
FIG. 1 schematically shows a side view of a device according to the invention.

In the figures, in which identical parts are provided with the same reference numerals, 1 denotes a cylindrical hollow chamber, the axis of which is denoted by 2. Instead of a cylindrical hollow chamber, a conical hollow chamber, which tapers in the direction of the axis 2, or else a bell-shaped or mushroom-shaped or else conical, concave hollow chamber (FIGS. 5a to 5d) or else a hollow chamber of any desired shaped may also be used.

Figure 6:
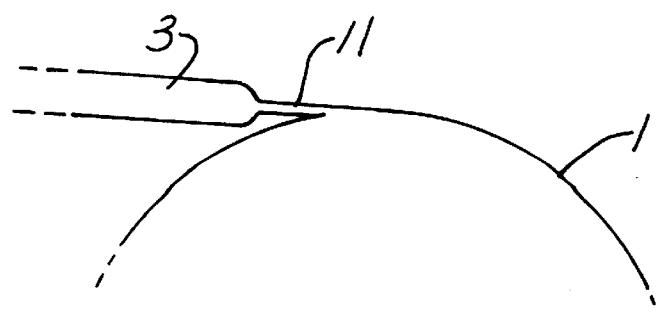
FIG. 6 shows a top plan view of part of the hollow chamber with the nozzle.

At one end of the hollow chamber 1, a feed duct 3, running in a plane arranged essentially perpendicularly to the axis 2, opens into a short nozzle 11 in such a way that the fluid mixed with the solid particles which is introduced through the feed duct 3 into the hollow chamber 1 hits the inside wall of the hollow chamber 1 tangentially. In order to introduce this fluid into the upper section of the chamber 1 at a given, relatively high rate, an arrangement 4 for increasing the pressure of the fluid, in particular a pump 4, and a nozzle 11 (FIG. 6), which is preferably integrated into the hollow chamber, are provided in the feed duct 3. The nozzle 11 may have a round or elongated cross section, in order in this way to produce the desired, laminar, helical flow of the fluid on the inside wall of the hollow chamber up to its other end. On account of the high pressure of the fluid introduced into the hollow chamber, the separation takes place in any position of the device.

Figure 2:
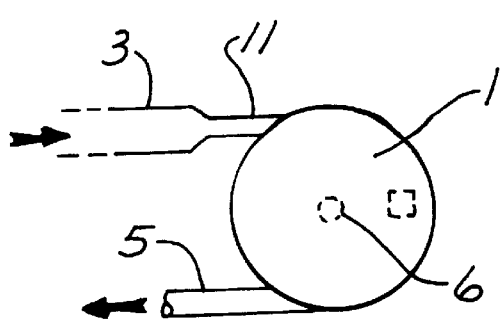
FIG. 2 shows a plan view of this device.

Provided at the other end of the hollow chamber 1 is a first discharge duct 5, which runs in a plane arranged essentially perpendicularly to the axis 2 and from which the dense particles, for example dense, heavy blood constituents, emerge once separation has taken place. This discharge duct 5 opens into the other end of the hollow chamber 1, likewise tangentially, as FIG. 2 shows in particular, to be precise offset with respect to the feed duct 3.

Also provided at this other end of the hollow chamber 1 is a second discharge duct 6, which extends essentially in a plane arranged parallel to the axis 2 or containing the axis 2. This second discharge duct 6 serves for the removal of the fluid freed of the dense particles contained in the fluid, for example the less dense blood plasma. The discharge ducts may be straight or curved.

FIG. 1 also shows that in the lower section of the hollow chamber 1 there is provided a measuring device 9, which is connected to a control arrangement 10, which in turn is connected to an arrangement 8 for changing the cross section of the discharge duct 5 and an arrangement 12 for changing the cross section of the discharge duct 6. The measuring device 9, in particular an optical sensor, in this case establishes the degree of separation at the other end of the hollow chamber 1, if the limit between the solid separated particles and the fluid shifts, the control arrangement 10 brings about a change in the passage cross section of the discharge duct 5 or the discharge duct 6 with the aid of the arrangements 8, 12. Since the amount of fluid fed in is equal to the sum of the amounts of constituents emerging from the two discharge ducts 5 and 6 and the location of optimum separation has been established, this ensures that as high a degree of separation as possible is maintained, i.e. that, in the case of whole blood being introduced into the hollow chamber 1, as high a proportion as possible of solid blood constituents is removed through the discharge duct 5, whereas the blood plasma freed of the solid blood constituents emerges from the discharge duct 6.

Figure 4:
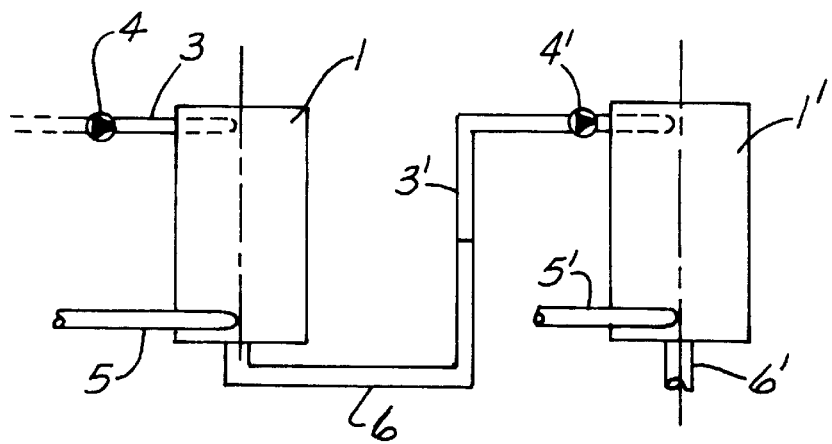
FIG. 4 shows a series of devices according to the invention arranged one after the other.

To increase the degree of separation, it is also possible to arrange a plurality of devices according to the invention one behind the other in cascade form, two such devices being schematically represented in FIG. 4; it can be seen from this figure that the discharge duct 6 of the separating arrangement 1 is connected to the discharge duct 3' of a downstream separating arrangement 1', so that fluid emerging from the discharge duct 6, already freed of a large part of the dense particles, is subjected to a further separation step in the adjoining separating arrangement 1'. It is also possible to dispense with the pumps 4, 4' of the devices.

Figures 5A, 5B, 5C, 5D:
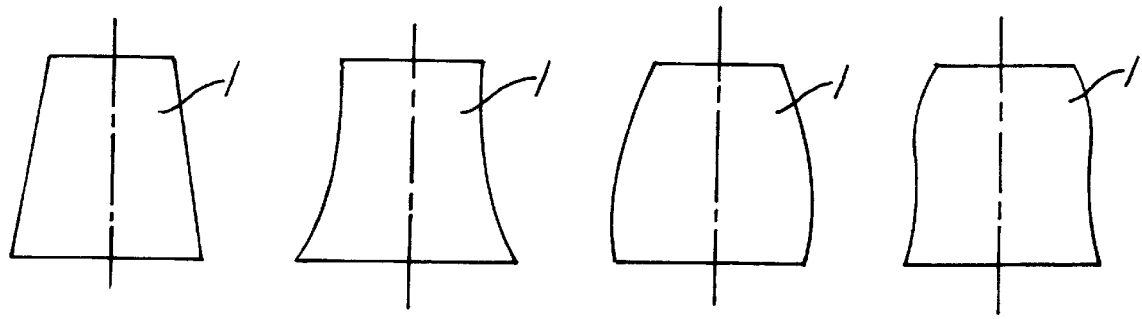
FIGS. 5a–5d shows elevation views of various configurations of the hollow chamber.

FIG. 5a shows that the form of the hollow chamber 1 may be conical, FIG. 5b shows that the form may be conical with a concave wall, FIG. 5c shows that the form may be mushroom-shaped and FIG. 5d shows that the form may be bell-shaped. Any desired, rotationally symmetrical forms are possible.

The method according to the invention for separating, in particular whole blood, using the device represented, thus comprises introducing the blood at a given, high rate tangentially into the upper section of a hollow chamber through the feed duct 3 and the nozzle 11, the cross-sectional area of which is smaller than that of the feed duct 3, so that the desired separation occurs on account of the laminar, helical flow on the inside wall of the hollow chamber 1 on the way between one end and the other end, the dense constituents being removed through the tangentially opening discharge duct 5, while the fluid freed of these particles, i.e. the blood plasma, is removed through the approximately centrally opening discharge duct 6.

An increase in the degree of separation is possible by arranging a plurality of devices according to the invention one behind the other in cascade form, so that the fluid emerging from the first separating arrangement can also be freed of the last dense particles by one or more further treatment steps. It goes without saying that the device represented and the method represented are not restricted to the treatment of blood, but are suitable for a wide range of biological fluids which have dense suspended or emulsified particles, such as milk for example.

Figure 3:
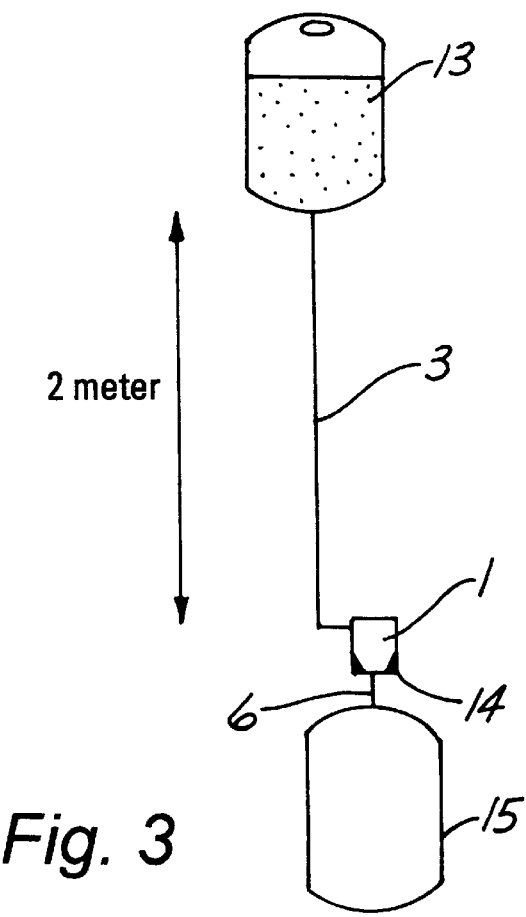
FIG. 3 shows a schematic representation of a leucocyte filter with the device according to the invention.

In FIG. 3, the device according to the invention is represented as a leucocyte filter. The blood contained in a blood bag 13 flows through the feed duct 3 under pressure into the hollow chamber 1, the leucocytes 14 being separated and remaining in the separating arrangement when the discharge duct 5 is closed. The blood freed of leucocytes emerges through the discharge duct 6 and is collected in a further bag 15. In this case too, it is possible to dispense with the pump, relying on gravity alone.

Although the device according to the invention has been described in the above figures with particular reference to the first embodiment mentioned above, it should be understood that it can be part as well of a device like those disclosed in EP 99810294 1 and EP 99810295.8 cited above.

What is claimed is:

1. A device for separating dense particles contained in blood or one or more proteins contained in blood plasma by means of a separating arrangement, comprising:

one feed duct, at least two discharge ducts, a pump for producing a pressure in order to introduce the blood or blood plasma into the separating device, a measuring device provided with the discharge ducts, a control arrangement connected to the measuring device, and a respective arrangement changing the cross section of a least one of the two discharge ducts and connected to the control arrangement.

2. The device according to claim 1, wherein the respective arrangement is changing the cross section of one of the two discharge ducts.

3. The device according to claim 2 in which the measuring device is sensing the separation level.

4. The device according to claim 3, in which the measuring device is an optical sensor.

5. The device according to claim 3, wherein the separating arrangement has one of the discharge ducts in each case being connected to the feed duct of the separating device following, as seen in the direction of flow of the fluid, and the discharge ducts connected to the following separating device having a pump or no pump.

6. The device according to claim 2, wherein the separating arrangement has one of the discharge ducts in each case being connected to the feed duct of the separating device following, as seen in the direction of flow of the fluid, and the discharge ducts connected to the following separating device having a pump or no pump.

7. The device according to claim 1, wherein the respective arrangement is changing the cross section of both the discharging ducts.

8. The device according to claim 7 in which the measuring device is sensing the separation level.

9. The device according to claim 8, in which the measuring device is an optical sensor.

10. The device according to claim 8, wherein the separating arrangement has one of the discharge ducts in each case being connected to the feed duct of the separating device following, as seen in the direction of flow of the fluid, and the discharge ducts connected to the following separating device having a pump or no pump.

11. The device according to claim 7, wherein the separating arrangement has one of the discharge ducts in each case being connected to the feed duct of the separating device following, as seen in the direction of flow of the fluid, and the discharge ducts connected to the following separating device having a pump or no pump.

12. The device according to claim 1 in which the measuring device is sensing the separation level.

13. The device according to claim 12, in which the measuring device is an optical sensor.

14. The device according to claim 13, wherein the separating arrangement has one of the discharge ducts in each case being connected to the feed duct of the separating device following, as seen in the direction of flow of the fluid, and the discharge ducts connected to the following separating device having a pump or no pump.

15. The device according to claim 12, wherein the separating arrangement has one of the discharge ducts in each case being connected to the feed duct of the separating device following, as seen in the direction of flow of the fluid, and the discharge ducts connected to the following separating device having a pump or no pump.

16. The device according to claim 1, wherein the separating arrangement has one of the discharge ducts in each case being connected to the feed duct of the separating device following, as seen in the direction of flow of the fluid, and the discharge ducts connected to the following separating device having a pump or no pump.

17. A device for separating dense particles contained in blood or one or more proteins contained in blood plasma by means of a separating arrangement, comprising:

at least one rotationally symmetrical stationary hollow chamber, at lease one feed duct, the feed duct running in a plane arranged essentially perpendicularly to the axis of the hollow chamber and opening tangentially into the upper end of the hollow chamber, at least two discharge ducts, a first discharge duct opening tangentially into the lower end of the hollow chamber and running in a plane arranged essentially perpendicularly to the axis of the hollow chamber and a second discharge duct opening into the lower section of the hollow chamber and arranged axially to the axis, an end of the discharge duct, designed as a tapering nozzle, opening into the upper end of the hollow chamber and integrated into the hollow chamber, a pump for producing a pressure in order to introduce the blood or blood plasma at a given pressure through the nozzle tangentially into the upper end of the hollow chamber, so that a laminar flow is formed in it, a measuring device connected to the ends of the hollow chamber provided with the discharge ducts, a control arrangement connected to the measuring device, and a respective arrangement changing the cross section of one or both discharge ducts and connected to the control arrangement.

18. The device according to claim 17, in which the respective arrangement is changing the cross section of both discharge ducts.

19. A method for separating dense particles contained in blood or one or more proteins contained in blood plasma using a device according to one or more of the preceding claims, comprising the steps of:

the whole blood or the plasma is introduced into the separating device though the feed duct at a pressure produced by the pump, the degree of separation is established by means of the measuring device, the control arrangement brings about a change in the passage cross section of one or both discharge ducts with the aid of the arrangement changing the cross section of the discharge ducts if the limit between the dense particles and the blood or the proteins of the plasma shifts, so that it is ensured that the amount of blood or plasma fed in is equal to the sum of the amounts of the constituents emerging from the two discharge lines, and a high degree of separation is thus maintained.

20. The method according to claim 19, wherein a plurality of separating arrangements are arranged one behind the other in the manner of a cascade in such a way that the blood or plasma flows successively through the separating arrangements for producing the degree of the separation.

* * * * *